United States Patent
Pugia et al.

(10) Patent No.: US 7,125,711 B2
(45) Date of Patent: Oct. 24, 2006

(54) METHOD AND APPARATUS FOR SPLITTING OF SPECIMENS INTO MULTIPLE CHANNELS OF A MICROFLUIDIC DEVICE

(75) Inventors: Michael J. Pugia, Granger, IN (US); James A. Profitt, Goshen, IN (US); Gert Blankenstein, Dortmund (DE); Ralf-Peter Peters, Dortmund (DE)

(73) Assignee: Bayer Healthcare LLC, Tarrytown, NY (US)

(*) Notice: Subject to any disclaimer, the term of this patent is extended or adjusted under 35 U.S.C. 154(b) by 31 days.

(21) Appl. No.: 10/326,157

(22) Filed: Dec. 19, 2002

(65) Prior Publication Data
US 2004/0121450 A1 Jun. 24, 2004

(51) Int. Cl.
C12M 1/34 (2006.01)
C12M 3/00 (2006.01)

(52) U.S. Cl. .............................. 435/288.5; 435/287.1; 435/287.3; 435/288.3; 435/288.4; 422/50; 422/55; 422/63; 422/81

(58) Field of Classification Search .................. 422/81, 422/58, 72, 100, 50, 68.1, 82.05, 55, 61, 422/63; 436/45, 180, 518, 164, 165, 166, 436/172; 435/283.1, 287.1, 288.7, 288.5, 435/7.1, 287.3, 288.4
See application file for complete search history.

(56) References Cited

U.S. PATENT DOCUMENTS

| | | | |
|---|---|---|---|
| 3,798,459 A | 3/1974 | Anderson et al. ........... 250/218 |
| 3,799,742 A * | 3/1974 | Coleman ...................... 422/61 |
| 3,804,533 A | 4/1974 | Scott ........................... 356/197 |
| 3,856,649 A | 12/1974 | Genshaw et al. ........... 204/195 |
| 3,992,158 A | 11/1976 | Przybylowicz et al. . 23/253 TP |
| 4,233,029 A | 11/1980 | Columbus .................. 23/230 R |
| 4,310,399 A | 1/1982 | Columbus ............... 204/195 R |
| 4,413,407 A | 11/1983 | Columbus ..................... 29/825 |
| 4,446,232 A | 5/1984 | Liotta ............................. 435/7 |
| 4,515,889 A | 5/1985 | Klose et al. .................... 435/4 |
| 4,534,659 A | 8/1985 | Dourdeville et al. ........ 366/338 |
| 4,587,220 A | 5/1986 | Mayambala-Mwanika et al. ............................ 436/66 |
| 4,600,507 A | 7/1986 | Shimizu et al. ............... 210/94 |
| 4,601,881 A * | 7/1986 | Webster ........................ 422/67 |
| 4,618,476 A | 10/1986 | Columbus .................... 422/100 |
| 4,647,654 A | 3/1987 | Knowles et al. ............ 530/326 |
| 4,658,022 A | 4/1987 | Knowles et al. ............ 530/402 |
| 4,676,274 A | 6/1987 | Brown ........................ 137/806 |
| 4,727,036 A | 2/1988 | Knowles et al. ............ 436/547 |
| 4,755,472 A | 7/1988 | Ismail et al. .................. 436/66 |
| 4,761,381 A | 8/1988 | Blatt et al. .................. 436/165 |
| 4,806,311 A | 2/1989 | Greenquist .................... 422/56 |
| 4,908,112 A | 3/1990 | Pace ........................... 204/299 |
| 4,963,498 A | 10/1990 | Hillman et al. ............... 436/69 |
| 4,968,742 A | 11/1990 | Lewis et al. ................ 525/54.1 |
| 4,970,171 A | 11/1990 | Messenger et al. ........... 436/66 |

(Continued)

FOREIGN PATENT DOCUMENTS

CA 2323424 3/2005

(Continued)

*Primary Examiner*—Long V. Le
*Assistant Examiner*—Melanie Yu

(57) ABSTRACT

A microliter liquid sample, particularly a biological sample, is analyzed in a device employing centrifugal and capillary forces. The sample is moved by capillary forces into one or more metering wells which define the amount of the sample to be analyzed in subsequent steps. The defined amount of the sample is transferred from the metering wells to one or more conditioning and reagent wells for measuring the amount of an analyte contained in each metered amount of the sample.

30 Claims, 8 Drawing Sheets

U.S. PATENT DOCUMENTS

| | | | |
|---|---|---|---|
| 5,024,647 A | 6/1991 | Jubin et al. ................... 494/37 |
| 5,053,197 A | 10/1991 | Bowen ........................ 422/58 |
| 5,089,420 A | 2/1992 | Albarella et al. ............ 436/66 |
| 5,096,836 A | 3/1992 | Macho et al. ............... 436/169 |
| 5,110,555 A | 5/1992 | Moore et al. ............... 422/100 |
| 5,141,868 A | 8/1992 | Shanks et al. .............. 435/288 |
| 5,151,369 A | 9/1992 | Lewis et al. ................. 436/67 |
| 5,160,702 A | 11/1992 | Kopf-Sill et al. ............. 422/72 |
| 5,164,598 A * | 11/1992 | Hillman et al. .......... 250/341.3 |
| 5,180,480 A | 1/1993 | Manz ..................... 204/299 R |
| 5,187,104 A | 2/1993 | Corey et al. ................. 436/86 |
| 5,202,261 A | 4/1993 | Musho et al. ............... 435/288 |
| 5,208,163 A | 5/1993 | Charlton et al. .............. 436/63 |
| 5,222,808 A | 6/1993 | Sugarman et al. .......... 366/274 |
| 5,250,439 A | 10/1993 | Musho et al. ............... 435/25 |
| 5,258,311 A | 11/1993 | Lewis et al. ................. 436/63 |
| 5,279,790 A | 1/1994 | Corey et al. ............. 422/55.57 |
| 5,286,454 A | 2/1994 | Nilsson et al. ............. 422/102 |
| 5,296,192 A | 3/1994 | Carroll et al. ................ 422/56 |
| 5,318,894 A | 6/1994 | Pugia ........................ 435/28 |
| 5,360,595 A | 11/1994 | Bell et al. .................. 422/56 |
| 5,372,918 A | 12/1994 | Usui et al. ................... 430/379 |
| 5,424,125 A | 6/1995 | Ballard et al. .............. 428/364 |
| 5,443,890 A | 8/1995 | Öhman ........................ 428/167 |
| 5,458,852 A | 10/1995 | Buechler ..................... 422/58 |
| 5,478,751 A | 12/1995 | Oosta et al. ................ 436/165 |
| 5,585,069 A | 12/1996 | Zanzucchi et al. .......... 422/100 |
| 5,631,303 A | 5/1997 | Reinecke .................... 521/40.5 |
| 5,700,695 A * | 12/1997 | Yassinzadeh et al. ....... 436/180 |
| 5,716,741 A | 2/1998 | Reinecke et al. .............. 430/8 |
| 5,716,851 A | 2/1998 | Pugia et al. ................. 436/86 |
| 5,826,981 A | 10/1998 | Fowler et al. ............... 366/337 |
| 5,834,314 A | 11/1998 | Gates et al. ................. 436/52 |
| 5,837,200 A | 11/1998 | Diessel et al. ................ 422/73 |
| 5,842,787 A | 12/1998 | Kopf-Sill et al. ........... 366/340 |
| 5,851,776 A | 12/1998 | Valkirs ....................... 435/7.1 |
| 5,866,345 A * | 2/1999 | Wilding et al. ............. 435/7.21 |
| 5,885,527 A | 3/1999 | Buechler ..................... 422/58 |
| 5,912,134 A * | 6/1999 | Shartle ....................... 435/7.24 |
| 5,921,678 A | 7/1999 | Desai et al. ................. 366/336 |
| 5,922,615 A | 7/1999 | Nowakowski et al. ....... 436/518 |
| 5,932,315 A | 8/1999 | Lum et al. ................... 428/172 |
| 5,939,272 A | 8/1999 | Buechler et al. ............. 435/7.1 |
| 5,942,443 A | 8/1999 | Parce et al. ................. 436/514 |
| 5,948,227 A | 9/1999 | Dubrow ...................... 204/455 |
| 5,955,028 A | 9/1999 | Chow ......................... 422/63 |
| 5,957,579 A | 9/1999 | Kopf-Sill et al. ........... 366/340 |
| 5,958,203 A | 9/1999 | Parce et al. ................. 204/451 |
| 5,958,694 A | 9/1999 | Nikiforov .................... 435/6 |
| 5,959,291 A | 9/1999 | Jensen ..................... 250/214 R |
| 5,964,995 A | 10/1999 | Nikiforov et al. .......... 204/450 |
| 5,965,001 A | 10/1999 | Chow et al. ................ 204/600 |
| 5,965,375 A | 10/1999 | Valkirs ....................... 435/7.2 |
| 5,965,410 A | 10/1999 | Chow et al. ................ 435/91.2 |
| 5,972,187 A | 10/1999 | Parce et al. ................. 204/453 |
| 5,976,336 A | 11/1999 | Dubrow et al. .............. 204/453 |
| 5,985,579 A | 11/1999 | Buechler et al. ............. 435/7.1 |
| 5,989,402 A | 11/1999 | Chow et al. ................ 204/601 |
| 5,994,150 A | 11/1999 | Challener et al. ............ 436/518 |
| 6,001,231 A | 12/1999 | Kopf-Sill .................... 204/454 |
| 6,002,475 A * | 12/1999 | Boyd et al. ................. 356/246 |
| 6,004,515 A | 12/1999 | Parce et al. ................. 422/100 |
| 6,011,252 A | 1/2000 | Jensen ..................... 250/214 R |
| 6,012,902 A | 1/2000 | Parce ........................ 417/48 |
| 6,019,944 A | 2/2000 | Buechler ..................... 422/58 |
| 6,024,138 A | 2/2000 | Fritz et al. .................... 141/31 |
| 6,030,581 A * | 2/2000 | Virtanen ..................... 422/68.1 |
| 6,037,455 A | 3/2000 | Buechler .................... 530/404 |
| 6,042,709 A | 3/2000 | Parce et al. ................. 204/453 |
| 6,042,710 A | 3/2000 | Dubrow ...................... 204/454 |
| 6,043,043 A | 3/2000 | Yip ............................ 435/72 |
| 6,046,056 A | 4/2000 | Parce et al. ................. 436/514 |
| 6,048,498 A | 4/2000 | Kennedy ..................... 422/99 |
| 6,063,589 A | 5/2000 | Kellogg et al. ............... 435/24 |
| 6,065,864 A | 5/2000 | Evans et al. ................ 366/167.1 |
| 6,068,752 A | 5/2000 | Dubrow et al. .............. 204/604 |
| 6,071,478 A | 6/2000 | Chow ......................... 422/81 |
| 6,074,616 A | 6/2000 | Buechler et al. ............. 422/104 |
| 6,074,725 A | 6/2000 | Kennedy ..................... 428/188 |
| 6,080,295 A | 6/2000 | Parce et al. ................. 204/451 |
| 6,082,891 A | 7/2000 | Schubert et al. ............. 366/338 |
| 6,086,740 A | 7/2000 | Kennedy ..................... 204/601 |
| 6,086,825 A | 7/2000 | Sundberg et al. ............ 422/100 |
| 6,090,251 A | 7/2000 | Sundberg et al. ............ 204/453 |
| 6,100,099 A | 8/2000 | Gordon et al. ............... 436/518 |
| 6,100,541 A | 8/2000 | Nagle et al. ................. 250/573 |
| 6,106,779 A | 8/2000 | Buechler et al. ............. 422/55 |
| 6,107,044 A | 8/2000 | Nikiforov ..................... 435/6 |
| 6,113,855 A | 9/2000 | Buechler .................... 422/58 |
| 6,123,798 A | 9/2000 | Gandhi et al. .............. 156/292 |
| 6,129,826 A | 10/2000 | Nikiforov et al. .......... 204/450 |
| 6,130,098 A | 10/2000 | Handique et al. ........... 436/180 |
| 6,132,685 A | 10/2000 | Kercso et al. ............... 422/104 |
| 6,136,272 A | 10/2000 | Weigl et al. ............... 422/82.05 |
| 6,136,610 A | 10/2000 | Polito et al. ................. 436/514 |
| 6,143,247 A * | 11/2000 | Sheppard et al. .............. 422/63 |
| 6,143,248 A | 11/2000 | Kellogg et al. ............... 422/72 |
| 6,143,576 A | 11/2000 | Buechler .................... 436/518 |
| 6,148,508 A | 11/2000 | Wolk .......................... 29/825 |
| 6,149,870 A | 11/2000 | Parce et al. ................. 422/100 |
| 6,150,119 A | 11/2000 | Kopf-Sill et al. ............. 435/7.1 |
| 6,150,180 A | 11/2000 | Parce et al. ................. 436/514 |
| 6,156,270 A | 12/2000 | Buechler .................... 422/58 |
| 6,170,981 B1 | 1/2001 | Regnier et al. .............. 366/336 |
| 6,176,119 B1 | 1/2001 | Kintzig ...................... 73/53.01 |
| 6,176,991 B1 | 1/2001 | Nordman .................... 204/601 |
| 6,185,029 B1 * | 2/2001 | Ishihara ...................... 359/216 |
| 6,186,660 B1 | 2/2001 | Kopf-Sill et al. ........... 366/340 |
| 6,190,034 B1 | 2/2001 | Nielsen et al. .............. 366/336 |
| 6,207,000 B1 | 3/2001 | Schwobel et al. ........... 156/248 |
| 6,235,175 B1 | 5/2001 | Dubrow et al. .............. 204/453 |
| 6,238,538 B1 | 5/2001 | Parce et al. ................. 204/600 |
| 6,241,379 B1 | 6/2001 | Larsen ..................... 366/181.5 |
| 6,251,567 B1 | 6/2001 | Reinecke et al. ............ 430/325 |
| 6,254,754 B1 | 7/2001 | Ross et al. .................. 204/548 |
| 6,264,900 B1 | 7/2001 | Schubert et al. ............. 422/224 |
| 6,268,025 B1 | 7/2001 | Reinecke et al. ............ 427/581 |
| 6,271,040 B1 | 8/2001 | Buechler .................... 436/170 |
| 6,281,254 B1 | 8/2001 | Nakajima et al. ............. 516/53 |
| 6,284,113 B1 | 9/2001 | Bjornson et al. ............ 204/453 |
| 6,287,520 B1 | 9/2001 | Parce et al. ................. 422/100 |
| 6,296,020 B1 * | 10/2001 | McNeely et al. ............ 137/806 |
| 6,296,126 B1 | 10/2001 | Peters ........................ 210/456 |
| 6,319,469 B1 | 11/2001 | Mian et al. .................. 422/64 |
| 6,321,791 B1 | 11/2001 | Chow ......................... 137/833 |
| 6,322,683 B1 | 11/2001 | Wolk et al. .................. 204/600 |
| 6,344,326 B1 * | 2/2002 | Nelson et al. ................. 435/6 |
| 6,379,974 B1 | 4/2002 | Parce et al. ................. 436/180 |
| 6,399,361 B1 | 6/2002 | Brotherston et al. ..... 435/283.1 |
| 6,428,664 B1 | 8/2002 | Bhullar et al. ......... 204/406.03 |
| 6,457,854 B1 | 10/2002 | Koop et al. ................. 366/336 |
| 6,540,896 B1 | 4/2003 | Manz et al. ................. 204/451 |
| 6,582,662 B1 * | 6/2003 | Kellogg et al. ............... 422/72 |
| 6,601,613 B1 * | 8/2003 | McNeely et al. ............ 137/833 |
| 6,632,399 B1 | 10/2003 | Kellogg et al. ............... 422/72 |
| 6,653,625 B1 * | 11/2003 | Andersson et al. .......... 250/288 |
| 6,709,559 B1 | 3/2004 | Sundberg et al. ............ 204/604 |
| 6,734,401 B1 | 5/2004 | Bedingham et al. ........ 219/388 |
| 6,776,965 B1 | 8/2004 | Wyzgol et al. .............. 422/100 |
| 6,811,752 B1 | 11/2004 | Barbera-Guillem ......... 422/100 |
| 6,878,555 B1 * | 4/2005 | Andersson et al. ......... 436/180 |
| 6,919,058 B1 | 7/2005 | Andersson et al. |
| 6,953,550 B1 * | 10/2005 | Sheppard et al. ............. 422/63 |
| 2001/0037099 A1 | 11/2001 | Effenhauser ................. 604/352 |

| | | | | | |
|---|---|---|---|---|---|
| 2001/0042712 A1 | 11/2001 | Battrell et al. ............ 210/511 | EP | 0693 560 A2 | 7/1995 |
| 2001/0046453 A1 | 11/2001 | Weigl et al. ............. 422/102 | EP | 1 013 341 A3 | 1/2001 |
| 2001/0048637 A1 | 12/2001 | Weigl et al. ............. 366/341 | WO | WO 95/17965 A1 | 7/1995 |
| 2001/0048900 A1 | 12/2001 | Bardell et al. ............ 422/100 | WO | WO 97/00121 | 1/1997 |
| 2002/0015959 A1 | 2/2002 | Bardell et al. ............... 435/6 | WO | WO 97/01055 | 1/1997 |
| 2002/0023684 A1 | 2/2002 | Chow ..................... 137/833 | WO | WO 99/46045 A1 | 9/1999 |
| 2002/0048535 A1 | 4/2002 | Weigl et al. ............. 422/100 | WO | WO 00/21728 | 4/2000 |
| 2002/0058332 A1 | 5/2002 | Quake et al. .......... 435/288.3 | WO | WO 00/22436 | 4/2000 |
| 2002/0076350 A1 | 6/2002 | Weigl et al. ............... 422/58 | WO | WO 00/25921 | 5/2000 |
| 2002/0079219 A1 | 6/2002 | Zhao et al. ............... 204/451 | WO | WO 00/34781 A2 | 6/2000 |
| 2002/0097632 A1 | 7/2002 | Kellogg et al. ........... 366/220 | WO | WO 00/34781 A3 | 6/2000 |
| 2002/0097633 A1 | 7/2002 | O'Connor et al. ......... 366/336 | WO | WO 00/36416 A1 | 6/2000 |
| 2002/0098528 A1* | 7/2002 | Gordon et al. ........... 435/7.21 | WO | WO 01/12329 A1 | 2/2001 |
| 2002/0112961 A1 | 8/2002 | O'Connor et al. ......... 204/601 | WO | WO 01/14063 A1 | 3/2001 |
| 2002/0114738 A1 | 8/2002 | Wyzgol et al. ............ 422/100 | WO | WO 01/14116 A1 | 3/2001 |
| 2002/0172980 A1* | 11/2002 | Phan et al. ................ 435/7.1 | WO | WO 01/19586 A1 | 3/2001 |
| 2002/0196435 A1* | 12/2002 | Cohen et al. .............. 356/246 | WO | WO 01/24931 A1 | 4/2001 |
| 2003/0003464 A1* | 1/2003 | Phan et al. .................... 435/6 | WO | WO 01/54810 A1 | 8/2001 |
| 2003/0054376 A1* | 3/2003 | Mullis et al. .................. 435/6 | WO | WO 02/18053 A1 | 3/2002 |
| 2003/0073089 A1* | 4/2003 | Mauze et al. ................... 435/6 | WO | WO 02/28532 | 4/2002 |
| 2004/0109793 A1* | 6/2004 | McNeely et al. ........... 422/100 | WO | WO 02/028532 A3 | 4/2002 |

FOREIGN PATENT DOCUMENTS

EP         0287883 A1      4/1988

\* cited by examiner

METHOD AND APPARATUS FOR SPLITTING OF SPECIMENS INTO MULTIPLE CHANNELS OF A MICROFLUIDIC DEVICE

BACKGROUND OF THE INVENTION

This invention relates generally to the field of microfluidics, as applied to analysis of various biological and chemical compositions. More particularly, the invention provides methods and apparatus for carrying out analyses, using both imposed centrifugal forces and capillary forces resulting from the surface properties of the passageways in the apparatus To determine the presence (or absence) of, or the amount of an analyte, such as glucose, albumin, or bacteria in bodily or other fluids, a reagent device is generally used to assist a technician performing the analysis. Such reagent devices contain one or more reagent areas at which the technician can apply the sample fluid and then compare the result to a standard. For example, a reagent strip is dipped into the sample fluid and the strip changes color, the intensity or type of color being compared with a standard reference color chart.

Preparation of such devices is difficult when the sample has a complex composition, as many bodily fluids do. The component to be identified or measured may have to be converted to a suitable form before it can be detected by a reagent to provide a characteristic color. Other components in the sample fluid may interfere with the desired reaction and they must be separated from the sample or their effect neutralized. Sometimes, the reagents are incompatible with each other. In other cases, the sample must be pre-treated to concentrate the analyte of interest. These and other problems make it difficult to provide in a single device the reagents and other components which are needed for a particular assay. The art contains many examples of devices intended to overcome such problems and to provide the ability to analyze a fluid sample.

A different approach is to carry out a sequence of steps which prepare and analyze a sample, but without requiring a technician to do so. One way of doing this is by preparing a device which does the desired processes automatically, but by keeping the reagents separated, is able to avoid the problems just discussed.

Carrying out analysis may involve receiving a sample, selecting a desired amount of the sample, diluting or washing the sample, separating it into components, and carrying out reactions with the sample or its components. If one were to carry out such steps in a laboratory on large samples, it would generally be necessary for a technician to manually perform the necessary steps or if automated, equipment would be needed to move the sample and its components and to introduce reagents, wash liquids, diluents and the like. However, it is typical of biological assays that the samples are small and therefore it follows that the processing steps must be carried out in very small equipment. Scaling down laboratory equipment to the size needed for samples of about 0.02 to 50 μL is not feasible and a different approach is used. Small vessels connected by micron-size passageways are made by creating such features in plastic or other suitable substrates and covering the resulting substrate with another layer. The vessels may contain reagents added to them before the covering layer is applied. The passageways may also be treated as desired to make them wettable or non-wettable by the sample to be tested. The sample, its components, or other fluids may move through such passageways by capillary action when the walls are wetted or they are prevented from moving when the fluids do not wet the walls of the passageway. Thus, the capillary passageways can either move fluids or prevent their movement as if a valve were present. Another method of moving fluids through capillary passageways is by centrifugal force, which overcomes the resistance of non-wettable walls. This simple description provides an overview of microfluidic devices. Specific applications are provided in many patents, some of which will be mentioned below.

An extended discussion of some of the principles used in arranging the vessels and passageways for various types of analyses is provided in U.S. Pat. No. 6,143,248. Additional examples of applications of those principles may be found in U.S. Pat. No. 6,063,589. The microfluidic devices described in those two patents were to be disposed in disc form and rotated on equipment capable of providing varying degrees of centrifugal force as needed to move fluids from one vessel to another. Generally, a sample would be supplied close to the center of rotation and gradually increasing rotational speeds would be used to move the sample, or portions of it, into vessels disposed further away from the center of rotation. The patents describe how specific amounts of samples can be isolated for analysis, how the samples can be mixed with other fluids for washing or other purposes, and how samples can be separated into their components.

Other patents describe the use of electrodes for moving fluids by electro-osmosis, such as U.S. Pat. No. 4,908,112. Caliper Technology Corporation has a portfolio of patent on microfluidic devices in which fluids are moved by electromotive propulsion. Representative examples are U.S. Pat. Nos. 5,942,443; 5,965,001; and 5,976,336.

In U.S. Pat. No. 5,141,868 capillary action is used to draw a sample into a cavity where measurements of the sample can be made by electrodes positioned in the sample cavity.

In U.S. patent application Ser. No. 10/082,415, microfluidic devices were disclosed which have advantages over those previously available. One such device employs multiple U-shaped capillary loops to provide metered amounts of sample liquid for subsequent analysis.

The present inventors have sought an improved method of metering multiple portions of a liquid sample having advantages over the device shown in U.S. patent application Ser. No. 10/082,415. Their solution to the problem is described in detail below.

SUMMARY OF THE INVENTION

The invention may be generally characterized as an improved analytical device which employs microfluidic techniques to divide small biological samples for analysis in the device. Typically, such samples have volumes of about 0.3 to 2.0 μL, although they may range from 0.2 to 200 μL depending on the number of metering steps.

The analytical device of the invention typically is a small piece of thin plastic into which has been cut microliter sized wells for receiving sample liquids, the wells being interconnected by capillary passageways having a width of about 10 to 500 μm and a depth of at least 5 μm. The passageways may be made either hydrophobic or hydrophilic using known methods, as required by the properties of the sample fluid to be tested. The passageways may include two types of capillary stops, that is a narrow stop having hydrophobic walls and a wide stop having hydrophilic walls. The desired features are formed in a base portion of the chip, reagents are placed in the appropriate wells and then a top portion is applied to complete the chip.

By using multiple reagent wells connected by capillary passageways, sample fluids can be provided with many separate treatments in a predetermined sequence, thereby avoiding many of the problems which are difficult to overcome with conventional test strips. In a preferred embodiment, one sample well supplies a series of metering wells having volumes defining the amount of the sample to be analyzed. Each metering well is in fluid communication with one or more reagent wells and associated conditioning wells via capillary passageways containing capillary stops for preventing transfer of the sample liquid until overcome by application of an opposing force e.g., centrifugal force. The samples may be further divided by additional metering wells and thereafter further reacted in additional reagent wells and their associated conditioning wells.

DESCRIPTION OF THE PREFERRED EMBODIMENTS

Flow in Microchannels

Figure 1:
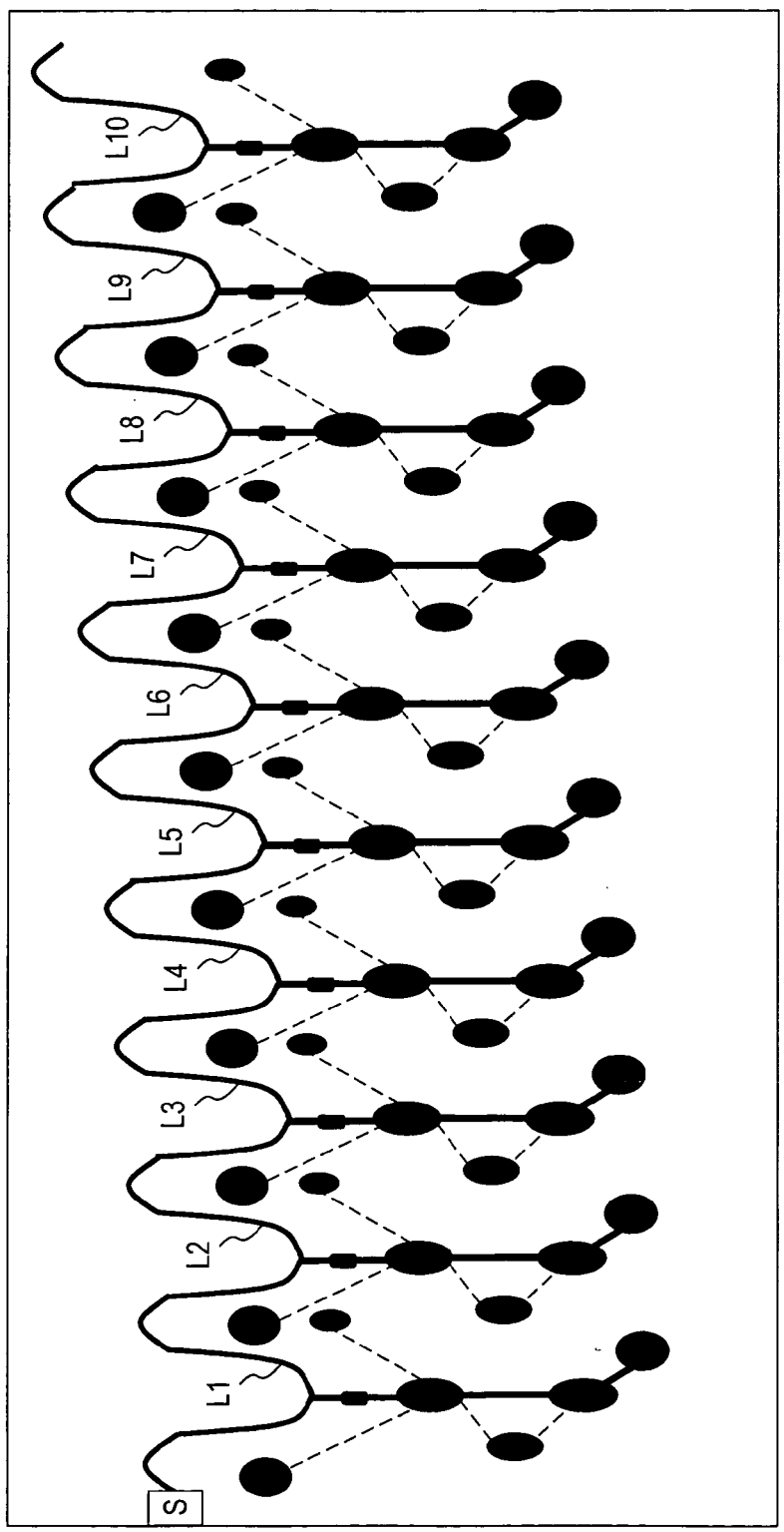
FIG. 1 illustrates an analytical device of U.S. patent application Ser. No. 10/082,415, in which ten samples can be analyzed.

The devices employing the invention typically use smaller channels than have been proposed by previous workers in the field. Another alternative used by others without using high pressure to move fluids (e.g., 100 psi or more) is the use of strong electrokinetic forces (e.g., 25 kV) to move fluids, a method which can damage biomolecules. In particular, the channels used in the invention have widths in the range of about 10 to 500 μm, preferably about 20–100 μm, whereas channels an order of magnitude larger have typically been used by others when capillary forces are used to move fluids. The minimum dimension for such channels is believed to be about 5 μm since smaller channels may effectively filter out components in the sample being analyzed. Generally, the depth of the channels will be less than the width. Channels in the range preferred in the invention make it possible to move liquid samples by capillary forces without the use of centrifugal force except to initiate flow. For example, it is possible to stop movement by capillary walls which are treated to become hydrophobic relative to the sample fluid. The resisting capillary forces can be overcome by a pressure difference, for example, by applying centrifugal force, pumping, vacuum, electro osmosis, or heating, preferably by centrifugal force. The pressure difference may be removed as liquid flow is established. Alternatively, if the capillary walls are treated to become hydrophilic relative to the sample fluid, the fluid will flow by capillary forces without the use of centrifugal or other force. If a hydrophilic stop is included in such a channel, then flow can be established by applying force to overcome the effect of the hydrophilic stop. As a result, liquids can be metered and moved from one region of the device to another as required for the analysis to be carried out.

A mathematical model has been derived which relates the centrifugal force, the fluid physical properties, the fluid surface tension, the surface energy of the capillary walls, the capillary size and the surface energy of particles contained in fluids to be analyzed. It is possible to predict the flow rate of a fluid through the capillary and the desired degree of hydrophobicity or hydrophilicity. The following general principles can be drawn from the relationship of these factors.

For any given passageway, the interaction of a liquid with the surface of the passageway may or may not have a significant effect on the movement of the liquid. When the surface to volume ratio of the passageway is large i.e. the cross-sectional area is small, the interactions between the liquid and the walls of the passageway become very significant. This is especially the case when one is concerned with passageways with nominal diameters less than about 200 μm, when capillary forces related to the surface energies of the liquid sample and the walls predominate. When the walls are wetted by the liquid, the liquid moves through the passageway without external forces being applied. Conversely, when the walls are not wetted by the liquid, the liquid attempts to withdraw from the passageway. These general tendencies can be employed to cause a liquid to move through a passageway or to stop moving at the junction with another passageway having a different cross-sectional area. If the liquid is at rest, then it can be moved by a pressure difference, such as by applying centrifugal force. Alternatively other means could be used, including air pressure, vacuum, electroosmosis, heating and the like, which are able to induce the needed pressure change at the junction between passageways having different cross-sectional areas or surface energies. In the present invention the passageways through which liquids move are smaller than have been used heretofore. This results in higher capillary forces being available and makes it possible to move liquids by capillary forces alone, without requiring external forces, except for short periods when a capillary stop must be overcome. However, the smaller passageways inherently are more likely to be sensitive to obstruction from particles in the biological samples or the reagents. Consequently, the surface energy of the passageway walls is adjusted as required for use with the sample fluid to be tested, e.g. blood, urine, and the like. This feature allows more flexible designs of analytical devices to be made. The devices can be smaller than the disks which have been used in the art and can operate with smaller samples. Other advantages will become evident from the description of the devices and the examples.

Analytical Devices of the Invention

The analytical devices of the invention may be referred to as "chips". They are generally small and flat, typically about 1 to 2 inches square (25 to 50 mm square) or disks having a radius of about 40 to 80 mm. The volume of samples will be small. For example, they will contain only about 0.3 to 2.0 μL for each assay, although the total volume of a specimen may range from 0.2 to 200 μL. The wells for the sample fluids will be relatively wide and shallow in order that the samples can be easily seen and measured by suitable equipment. The interconnecting capillary passageways will have a width in the range of 10 to 500 μm, preferably 20 to 100 μm, and the shape will be determined by the method used to form the passageways. The depth of the passageways should be at least 5 μm.

While there are several ways in which the capillaries and sample wells can be formed, such as injection molding, laser ablation, diamond milling or embossing, it is preferred to use injection molding in order to reduce the cost of the chips. Generally, a base portion of the chip will be cut to create the desired network of sample wells and capillaries and then a top portion will be attached over the base to complete the chip.

The chips are intended to be disposable after a single use. Consequently, they will be made of inexpensive materials to the extent possible, while being compatible with the reagents and the samples which are to be analyzed. In most instances, the chips will be made of plastics such as polycarbonate, polystyrene, polyacrylates, or polyurethene, alternatively, they can be made from silicates, glass, wax or metal.

The capillary passageways will be adjusted to be either hydrophobic or hydrophilic, properties which are defined with respect to the contact angle formed at a solid surface by a liquid sample or reagent. Typically, a surface is considered hydrophilic if the contact angle is less than 90 degrees and hydrophobic if the contact angle is greater than 90°. A surface can be treated to make it either hydrophobic or hydrophilic. Preferably, plasma induced polymerization is carried out at the surface of the passageways. The analytical devices of the invention may also be made with other methods used to control the surface energy of the capillary walls, such as coating with hydrophilic or hydrophobic materials, grafting, or corona treatments. In the present invention, it is preferred that the surface energy of the capillary walls is adjusted, i.e. the degree of hydrophilicity or hydrophobicity, for use with the intended sample fluid. For example, to prevent deposits on the walls of a hydrophobic passageway or to assure that none of the liquid is left in a passageway. For most passageways in the present invention the surface is considered to be generally hydrophilic since the liquid tends to wet the surface and the surface tension forces causes the liquid to flow in the passageway. For example, the surface energy of capillary passageways can be adjusted by known methods so that the contact angle of water is between 20° to 60° when the passageway is to contact whole blood or a contact angle of 25° to 80° when the passageway is to contact urine.

Movement of liquids through the capillaries typically is prevented by capillary stops, which, as the name suggests, prevent liquids from flowing through the capillary. If the capillary passageway is hydrophilic and promotes liquid flow, then a hydrophobic capillary stop can be used, i.e. a smaller passageway having hydrophobic walls. The liquid is not able to pass through the hydrophobic stop because the combination of the small size and the non-wettable walls results in a surface tension force which opposes the entry of the liquid. Alternatively, if the capillary is hydrophobic, no stop is necessary between a sample well and the capillary. The liquid in the sample well is prevented from entering the capillary until sufficient force is applied, such as by centrifugal force, to cause the liquid to overcome the opposing surface tension force and to pass through the hydrophobic passageway. It is a feature of the present invention that the centrifugal force is only needed to start the flow of liquid. Once the walls of the hydrophobic passageway are fully in contact with the liquid, the opposing force is reduced because presence of liquid lowers the energy barrier associated with the hydrophobic surface. Consequently, the liquid no longer requires centrifugal force in order to flow. While not required, it may be convenient in some instances to continue applying centrifugal force while liquid flows through the capillary passageways in order to facilitate rapid analysis.

When the capillary passageways are hydrophilic, a sample liquid (presumed to be aqueous) will naturally flow through the capillary without requiring additional force. If a capillary stop is needed, one alternative is to use a narrower hydrophobic section which can serve as a stop as described above. A hydrophilic stop can also be used, even through the capillary is hydrophilic. Such a stop is wider than the capillary and thus the liquid's surface tension creates a lower force promoting flow of liquid. If the change in width between the capillary and the wider stop is sufficient, then the liquid will stop at the entrance to the capillary stop. It has been found that the liquid will eventually creep along the hydrophilic walls of the stop, but by proper design of the shape this movement can be delayed sufficiently so that stop is effective, even though the walls are hydrophilic.

When a hydrophobic stop is located in a hydrophilic capillary, a pressure difference must be applied to overcome the effect of the hydrophobic stop. In general, pressure difference needed is a function of the surface tension of the liquid, the cosine of its contact angle with the hydrophilic capillary and the change in dimensions of the capillary. That is, a liquid having a high surface tension will require less force to overcome a hydrophobic stop than a liquid having a lower surface tension. A liquid which wets the walls of the hydrophilic capillary, i.e. it has a low contact angle, will require more force to overcome the hydrophobic stop than a liquid which has a higher contact angle. The smaller the hydrophobic channel, the greater the force which must be applied.

In order to design chips in which centrifugal force is applied to overcome hydrophilic or hydrophobic stops, empirical tests can be used to provide useful information. For example, a chip was made having sample wells each connected by a hydrophobic capillary to a second well located further from the center of rotation. Colored water was placed in the sample wells and the chip rotated to apply centrifugal force to the sample. The centrifugal force applied is proportional to the radial distance from the center of rotation and the square of the rotational speed. When the rotational speed was sufficient, the water in a sample well entered the hydrophobic capillary and flowed to the second well. The following table summarizes the data obtained.

| | Radial distance to | | Capillary, μm | | Flow Begins |
|---------|----------------|--------------|-------|-------|-------------|
| Test No | Sample well (mm) | Second well/mm | Width | Depth | @ rpm |
| 1 | 24 | 28 | 30 | 10 | 2500 |
| 2 | 24 | 35 | 30 | 10 | 2500 |
| 3 | 24 | 35 | 100 | 10 | 1300 |
| 4 | 24 | 29 | 100 | 10 | 1300 |
| 5 | 33 | 38 | 30 | 10 | 1300 |
| 6 | 33 | 38 | 100 | 10 | 700 |

The following conclusions may be drawn from the above results.
- the length of the capillary does not affect the force required to initiate flow (Tests 1–2, 3–4).
- increasing the size of the capillary reduced the force required to initiate flow (Tests 2–3, 5–6).
- less force is required when the sample well is further from the center of rotation (Tests 1–5, 3–6).

Information provided by tests such as these enable one to arrange the position of liquid-containing wells on chips and size the interconnecting capillary channels so that liquid sample can be moved as required by providing the needed force by adjusting the rotation speed.

Figure 3A:
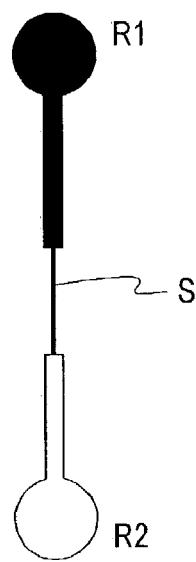
FIG. 3 illustrates hydrophobic and hydrophilic capillary stops.

FIGS. 3a & b illustrate a hydrophobic stop (a) and a hydrophilic stop (b) which may be used in analytical devices of the invention. In FIG. 3a well R1 is filled with liquid and the liquid extends through the attached hydrophilic capillary until the liquid is prevented from further movement by the narrow hydrophobic capillary passageways, which provide a surface tension force which prevents the liquid from entering the stop. If a force is applied from well R1 in the direction of the capillary stop the opposing force can be overcome and the liquid in R1 can be transferred to well R2. FIG. 3a can also represent a hydrophilic stop of the type discussed above in which an abrupt reduction in cross-section of hydrophilic passageways prevents liquid from entering until sufficient force is applied.

Figure 3B:
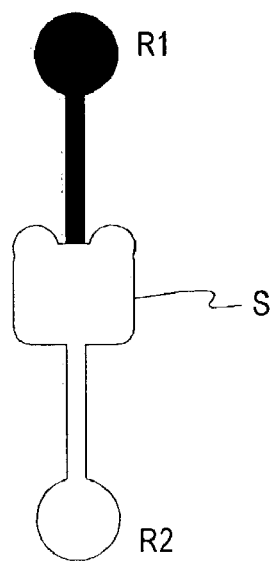

In FIG. 3b the capillary stop illustrated is a hydrophilic stop, which prevents the liquid in R1 from flowing through into well R2. In this case, the capillary stop is not narrow and it has hydrophilic walls. The increase in width of the channel and the shape of the stop prevent surface tension forces from causing liquid flow out of the attached capillary. However, as mentioned above, it has been found that liquid will gradually creep along the walls and overcome the stopping effect with the passage of enough time. For most analytical purposes, the stop serves its purpose since the time needed for analysis of a sample is short compared to the time needed for the liquid to overcome the stop by natural movement of the liquid.

FIG. 1 shows the multiple sample microfluidic chip of U.S. patent application Ser. No. 10/082,415. A single sample of liquid is introduced at sample well S, from which it flows by capillary forces through hydrophilic capillaries into ten sample loops L 1–10. The vent channels are not illustrated in FIG. 1, but will be provided to remove air from the upper portions of each loop so that they are completely filled with liquid. The liquid is stopped in each loop by hydrophilic stops. Then, when a force is applied to overcome the capillary stops, the liquid in each loop flows into the wells for analysis. This method of metering is effective, but has disadvantages. A capillary inherently contains a small volume of liquid. Thus, a capillary required to hold a sample is relatively long and occupies significant space on a chip. For example, a capillary passage 100 μm wide and 50 μm deep would be 100 mm long to hold a 0.5 μL sample, 200 mm long to hold 1 μL, and 400 mm long to hold 2 μL. Therefore a capillary metering channel would be most suitable for very small samples. Also, it has been found that it is difficult to assure that the capillary is completely emptied so that accuracy suffers.

In contrast, metering chambers of the present invention occupy much less area in an analytical chip. For example, a metering chamber 50 μm deep and 4 mm wide will have a length of 2.5 mm to hold a sample of 0.5 μL. A length of 5 mm is needed to hold a sample of 1 μL and 10 mm to hold a sample of 2 μL.

Figure 2:
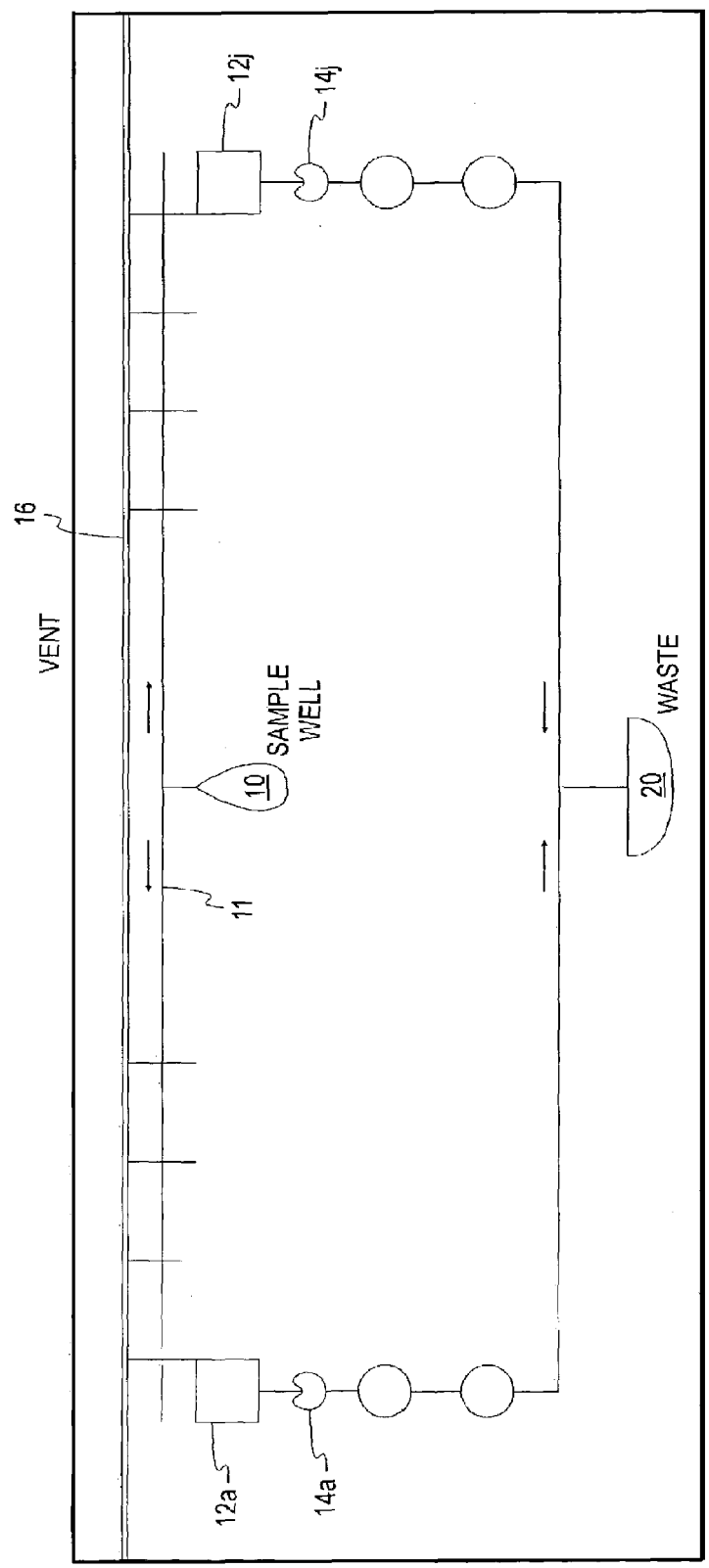
FIG. 2 illustrates one embodiment of the improved analytical device of the invention.

FIG. 2 shows an embodiment of the invention which also employs ten sample paths, as did the arrangement shown in FIG. 1. In this design, the sample is introduced into a single large sample well 10 in the middle of the chip, from which the sample moves by capillary forces into each often metering wells 12a–j that define the amount of the sample liquid to be analyzed by the chip in ten parallel steps. Thus, instead of using U-shaped capillary loops to define the volume of the sample, it is instead defined by the amount needed to fill a metering well. The metering wells are vented as shown to assure that each one is completely filled. The sample also fills the short portion of the capillary at the bottom of the metering well and is stopped by the hydrophilic stop 14a–j (as shown) or by a hydrophobic stop, previously described. This system has the advantage of providing more accurate definition of the sample size than the capillary loops of FIG. 1 and each of the metering wells are independent of the others. Also, it is more compact and therefore permits closer spacing of the sample channels so that more can be provided on any given chip size. It will be noted that the outlets of the reagent wells are commonly manifolded to empty into a single waste well 20. The operation of each sample channel can now be described with reference to FIG. 4.

Figure 4:
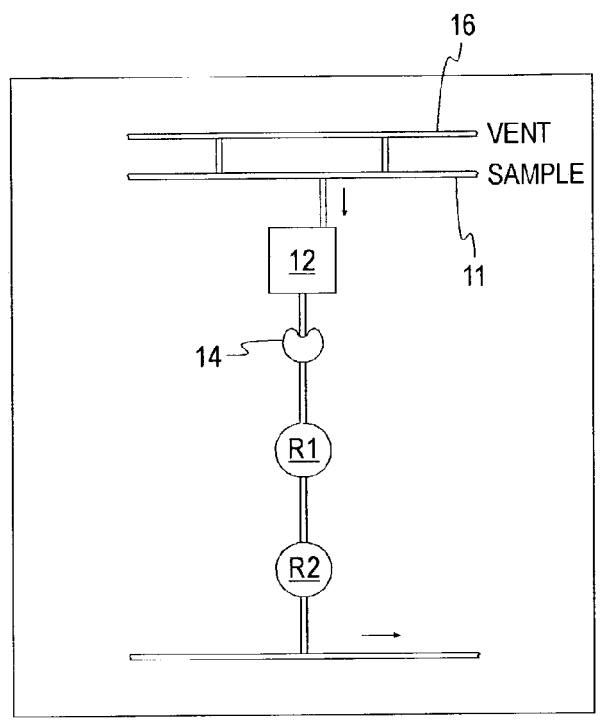
FIG. 4 shows one of the reaction channels of FIG. 2.

The single large sample well 10 shown in FIG. 2 supplies each of the metering wells 12a–j by movement through the capillary passageway 11, the walls of which are made hydrophilic in order to facilitate the transfer of the sample liquid. Each of the metering wells 12a–j is made to hold the amount of the sample required for the reactions with reagents in the downstream wells, R1 and R2. It will be understood that while two reaction wells are shown here, additional wells could be provided, for example by the those shown in U.S. patent application Ser. No. 10/082,415 and FIG. 5. As the metering well is filled, air is expelled through the vent channel 16 so that the metering well 12 is always filled to the maximum extent. Sample liquid is prevented from entering the vent channel by a hydrophilic or hydrophobic stop, such as have previously been described (not shown). In FIG. 4, a hydrophilic stop 14 is shown at the bottom of the metering well, which prevents the sample liquid from proceeding further until the effect of the stop is overcome by applying a force to the liquid in the metering well, e.g. centrifugal force. It is an advantage of the design shown that a capillary passageway extends from the outlet of the hydrophilic stop to the first reaction well R1. Thus, the sample is kept from any contact with the reagent in R1 until the sample is discharged from the metering well. The passageway typically will be made hydrophilic so that the sample is moved entirely into R1 once the stop is overcome. R1 can serve various purposes. For example, it can contain materials which condition the sample liquid for measurement of the analyte in R2. R1 may also contain a first reagent for measuring the first of two analytes, while R2 contains a second reagent for measuring a second analyte. Other possible uses for R1 and R2 include, but are not limited to, antibody capture areas, plasma, blood or particle separators, incubation areas, mixing areas, cell lysis areas, concentrators, washing areas, dilution areas, resuspension areas, optical or electrochemical detection wells with or without liquid or dry reagents. After the sample has been delivered from the metering well into R1, it is prevented from moving into R2 by using another fluid stop (not shown) or by making the capillary between R1 and R2 hydrophobic to act as stop. Such stops again can be overcome by application of a force, such as centrifugal force, in order to move the sample from R1 to R2. Again, the sample is prevented from moving from R2 by using a hydrophilic stop or by making the outlet capillary hydrophobic. After the reactions have been completed and measurement of the analyte(s) has taken place, the sample can be removed from R2 and passed to the waste well.

As can be appreciated, a single sample of liquid can be measured for any desired number of properties at the same time. For example, a sample of urine could be applied to a chip containing 10 parallel processing channels to test for the presence of nitrate, blood, albumin, specific gravity, creatinine, white blood cells, pH, glucose, ketone, and bacteria at the same time. A sample of blood could be analyzed for HbAlc (hemoglobin Aic), PSA, BNP (brain natruiuretic peptide), and high sensitivity CRP (c-reactive protein). Of course, the parallel processing channels need not be identical and different sequences of analytical steps could be undertaken.

Microfluidic devices of the invention can take many forms. A single sample can be divided into samples which have a predetermined size so that subsequent analytical procedures can provide an accurate measure of the analyte of interest. Analytical procedures may include conditioning of the metered sample by diluting the sample, prereacting the analyte to place it in better form for subsequent reactions, removing interfering components, mixing reagents, lysising cells, capturing bio molecules, enzymatic reactions, incubation for binding events, staining, or deposition. Such conditioning may be carried out before or during metering of the sample, or after metering before carrying out reactions which provide a measure of the analyte. In the discussion of alternative configurations of devices of the invention, wells may contain dry or liquid reagents or conditioning materials.

Figure 5:
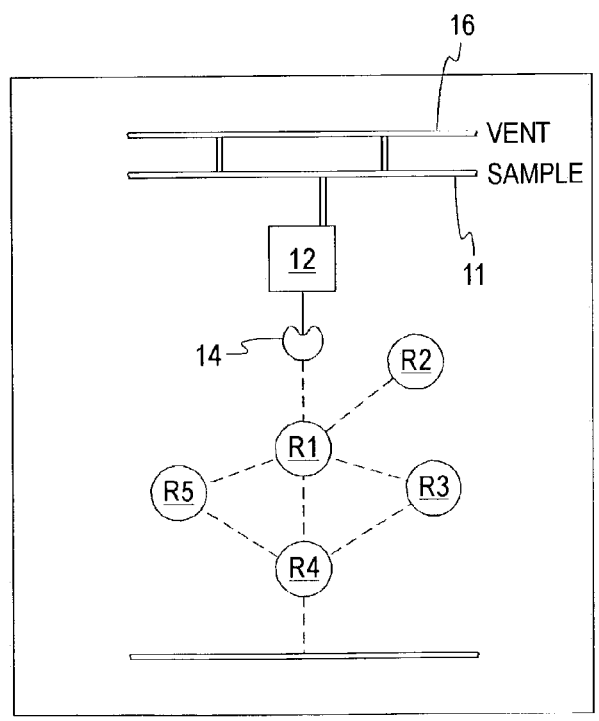
FIG. 5 shows a single reaction channel including auxiliary wells.

FIG. 5 shows a single reaction channel which permits a number of potential uses. The metering well 12 supplies a sample to reaction well R1, where various processes may occur, such as pretreatment of the sample by a reagent in R1 or with a reagent supplied from R2. The sample can be transferred to any or all of wells R3, R4, and R5, for further processing or detection of an analyte contained in the sample.

FIGS. 6–11 illustrate some of the many possible variations of the invention. In each a metering well 12 (or multiple wells 12a et seq) is included to supply a predetermined volume of the sample fluid to the reagent areas. The reagent wells area generally labeled "R" et seq.

Figure 6:
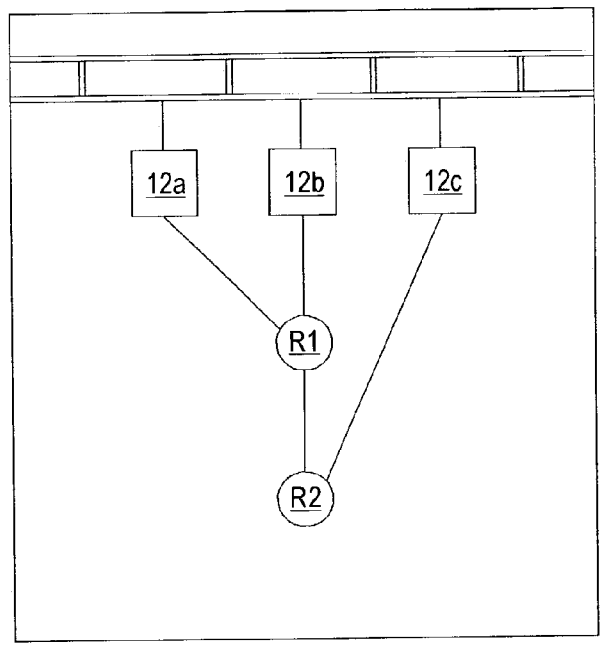
FIG. 6 illustrates an embodiment in which a sample is divided into three metering wells which supply two reaction chambers.

In FIG. 6, three measured sample are used to supply wells $R_1$ and $R_2$ in which the samples are treated or reacted. Note that one such well (12c) is arranged to supply a treated or reacted sample to a second well.

Figure 7:
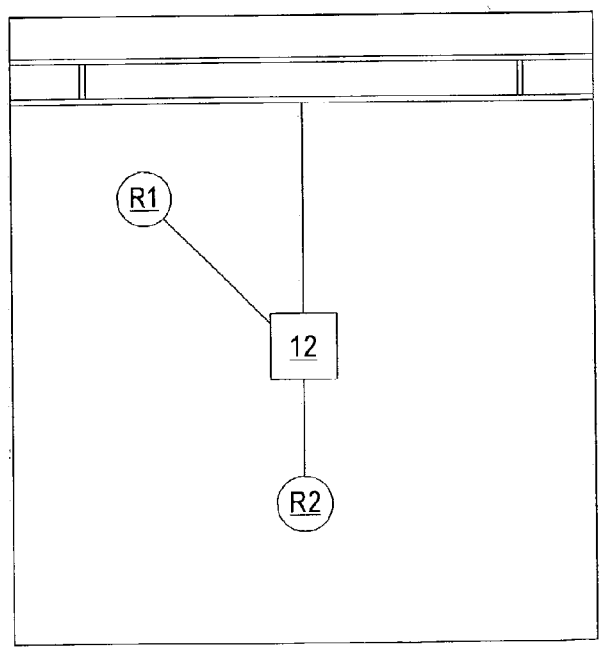
FIG. 7 illustrates an embodiment in which a reagent is supplied to the metering well.

FIG. 7 shows a single metering well 12 which is supplied from $R_1$ with a liquid reagent. The combined sample and reagent is subsequently transferred to a reagent well $R_2$ for a reaction which provides for detection of an analyte.

Figure 8:
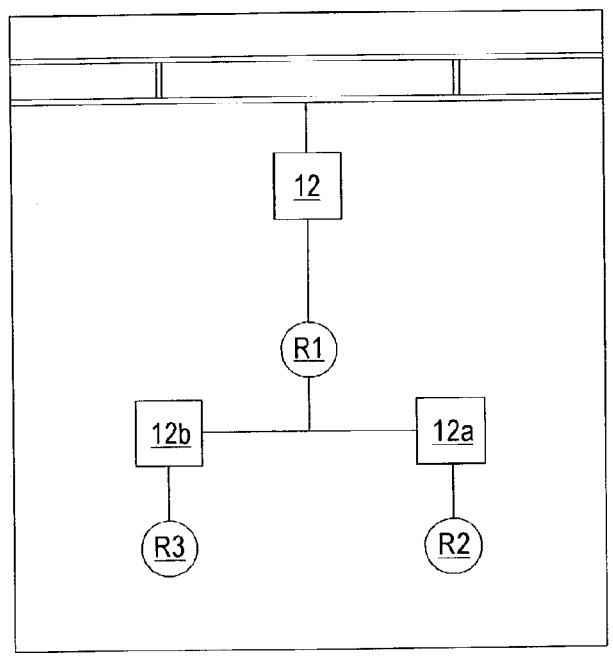
FIG. 8 illustrates an embodiment in which a sample is reacted, then subdivided and reacted a second time.

FIG. 8 illustrates an alternative in which a sample is metered in metering well 12 and then transferred to a reagent area $R_1$, then divided into two secondary samples in metering wells 12a and 12b and finally transferred to secondary reaction wells $R_2$ and $R_3$.

Figure 9:
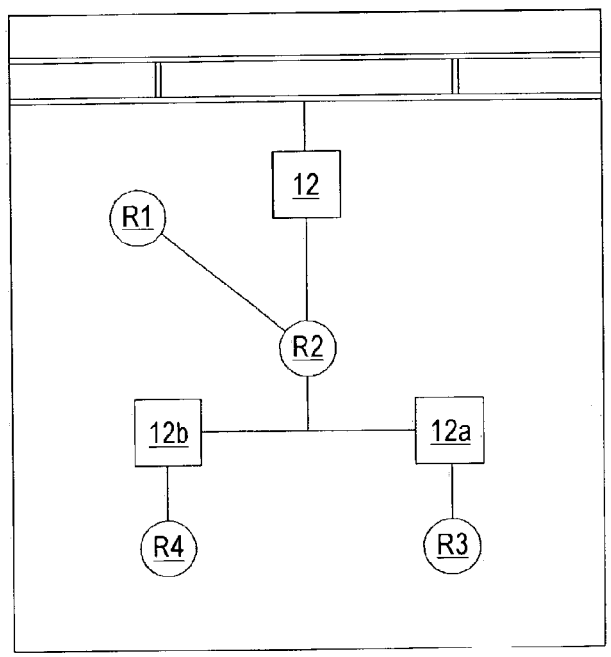
FIG. 9 shows a variation of FIG. 8 in which a reactant is supplied to a reaction chamber from a second chamber.

FIG. 9 shows an arrangement similar to FIG. 8 but with the addition of a liquid reagent well $R_1$ for transferring a liquid reagent to the first reaction well $R_2$.

Figure 10:
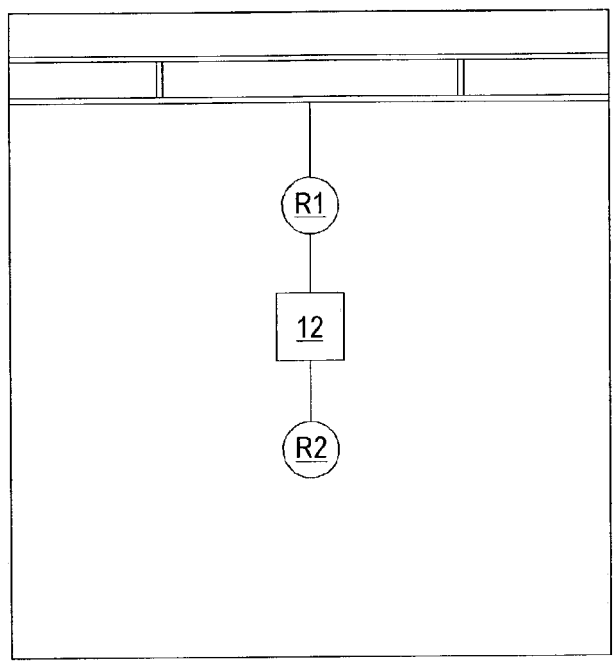
FIG. 10 illustrates an embodiment in which a sample is reacted before entering the metering well.

FIG. 10 illustrates an alternative in which a sample is first contacted with a first reagent in reagent well $R_1$ before being metered in metering well 12. Subsequently, the prereacted sample is transferred to reagent well $R_2$ for detection of an analyte.

Figure 11:
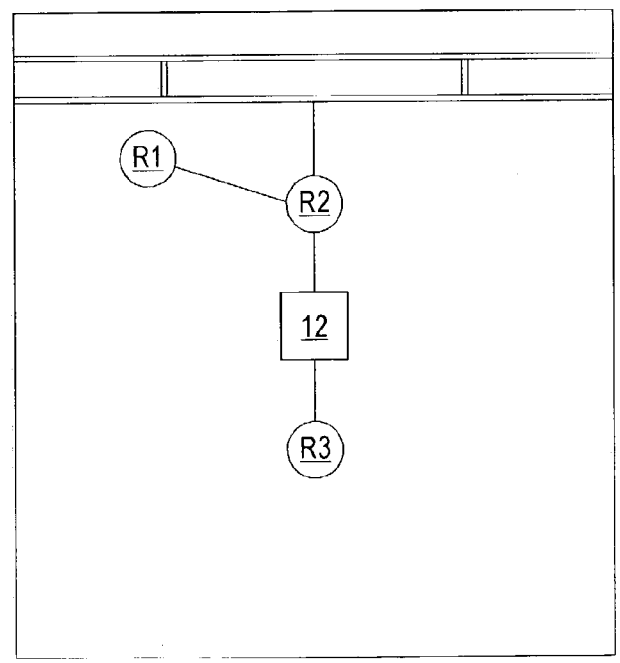
FIG. 11 is a variation of FIG. 10 in which a reactant is supplied to the pre-reaction well.

FIG. 11 shows still another variation, combining features of FIGS. 9 and 10. A liquid reagent is transferred from well $R_1$ to pretreatment well $R_2$ where it contacts a sample prior to metering well 12.

Figure 12:
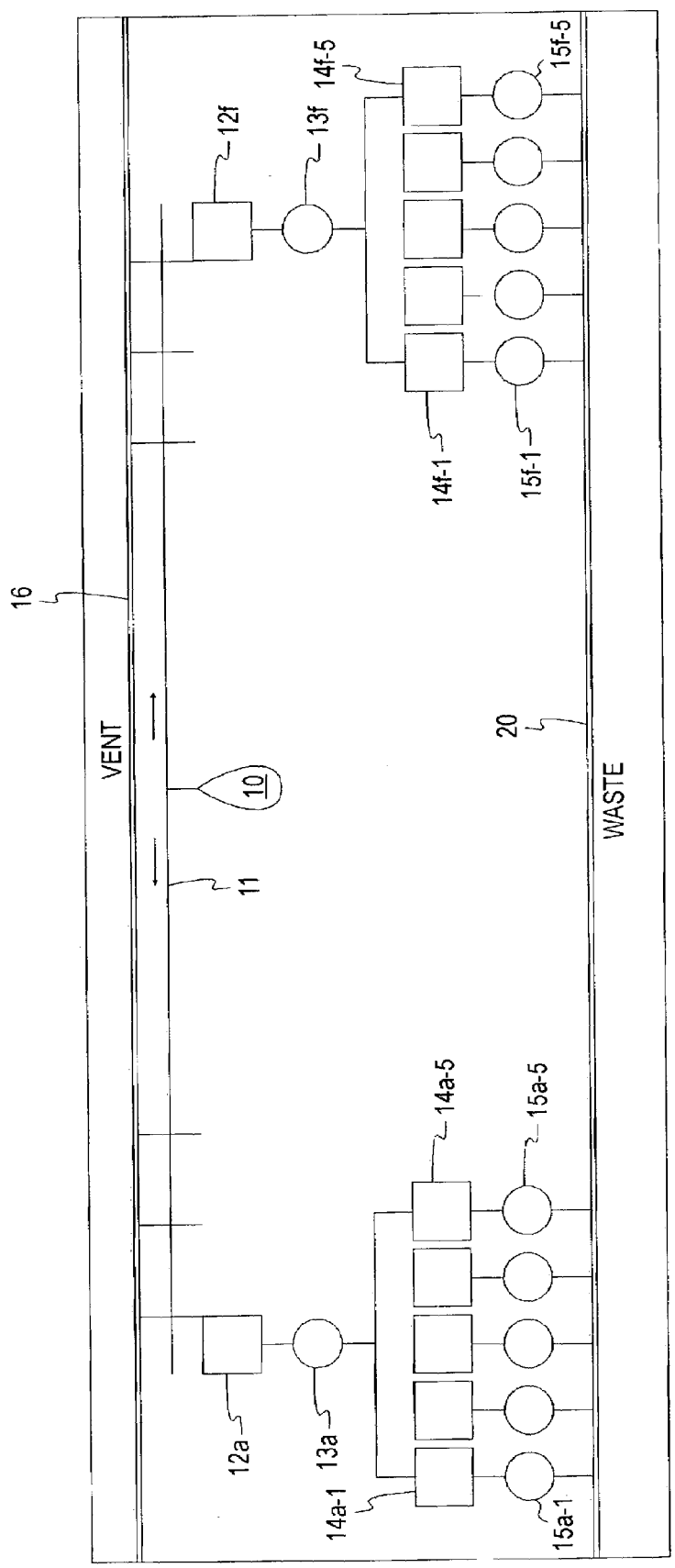
FIG. 12 shows a sample divided into multiple metering wells, each of which supplies a second set of metering wells and reaction chambers.

FIG. 12 is a variation of FIG. 2 in which first reaction wells 13a–f supply a reacted sample to multiple sub-metering wells 14a–f (1–5), which in turn supply samples to reaction wells 15a–f (1–5).

Applications

Microfluidic devices of the invention have many applications. Analyses may be carried out on samples of many biological fluids, including but not limited to blood, urine, water, saliva, spinal fluid, intestinal fluid, food, and blood plasma, blood and urine are of particular interest. A sample of the fluid of interest is deposited in the sample well and subsequently divided in metering wells into the amounts to be analyzed. The metered sample will be assayed for the analyte of interest, including for example a protein, a cell, a small organic molecule, or a metal. Examples of such proteins include albumin, HbAlc, protease, protease inhibitor, CRP, esterase, and BNP. Cells which may be analyzed include E. coli, pseudomonas, white blood cells, red blood cells, h. pylori, strep a, chlamdia, and mononucleosis. Metals which are to be detected include iron, manganese, sodium, potassium, lithium, calcium, and magnesium.

In many applications, color developed by the reaction of reagents with a sample is measured. It is also feasible to make electrical measurements of the sample, using electrodes positioned in the small wells in the chip. Examples of such analyses include electrochemical signal transducers based on amperometric, impedimetric, potentimetric detection methods. Examples include the detection of oxidative and reductive chemistries and the detection of binding events.

There are various reagent methods which could be used in chips of the invention. Reagents undergo changes whereby the intensity of the signal generated is proportional to the concentration of the analyte measured in the clinical specimen. These reagents contain indicator dyes, metals, enzymes, polymers, antibodies, electrochemically reactive ingredients and various other chemicals dried onto carriers. Carriers often used are papers, membranes or polymers with various sample uptake and transporting properties. They can be introduced into the reagent wells in the chips of the invention to overcome the problems encountered in analyses using reagent strips.

In contrast, reagent strips may use only one reagent area to contain all chemicals needed to generate color response to the analyte. Typical chemical reactions occurring in dry reagent strips can be grouped as dye binding, enzymatic, immunological, nucleotide, oxidation or reductive chemistries. In some cases, up to five competing and timed chemical reactions are occurring within one reagent layer a method for detecting blood in urine, is an example of multiple chemical reactions occurring in a single reagent. For example, analyte detecting reaction is based on the peroxidase-like activity of hemoglobin that catalyzes the oxidation of a indicator, 3,3',5,5'-tetramethyl-benzidine, by diisopropylbenzene dihydroperoxide. In the same pad, a second reaction occurs to remove ascorbic acid interference, based on the catalytic activity of a ferric-HETDA complex that catalyzes the oxidation of ascorbic acid by diisopropylbenzene dihydroperoxide.

Multiple reagent layers are often used to measure one analyte in reagent strips. Chemical reagent systems are placed into distinct reagent layers and provide for reaction separation steps such as chromatography and filtration. Whole blood glucose strips often use multiple reagent areas to trap intact red blood cells that interfere with the color generation layer. Immuno-chromatography strips are constructed with chemical reactions occurring in distinct reagent areas. The detection for human chorionic gonadotropin (hCG) or albumin is an example application of a strip with four reagent areas. The first reagent at the tip of the strip is for sample application and overlaps the next reagent area, providing for transfer of the patent sample (urine) to the first reagent area. The treated sample then migrates across a third reagent, where reactants are immobilized for color development. This migration is driven by a fourth reagent area that takes up the excess specimen. The chromatography reaction takes place in the third reagent area, called the test or capture zone, typically a nitrocellulose membrane. In the first and second layers, an analyte specific antibody reacts with the analyte in the specimen and is chromatographically transferred to the nitrocellulose membrane. The antibody is bound to colored latex particles as a label. If the sample contains the analyte, it reacts with the labeled antibody. In the capture zone, a second antibody is immobilized in a band and captures particles when analyte is present. A colored test line is formed. A second band of reagent is also immobilized in the capture zone to allow a control line to react with particles, forming color. Color at the control line is always formed when the test system is working properly, even in the absence of the hCG in the patient sample.

The albumin analyses described above can also be done by other methods. Proteins such as human serum albumin (HSA), gamma globulin (IgG) and Bence Jones (BJP) proteins can be determined in a variety of ways. The simplest is dye binding which relies on the color change of the dye as it binds protein. Many dyes have been used: Examples are 2 (4-hydroxyphenylazo)benzoic acid [HAPA], bromocresol green, bromocresol blue, bromophenol blue, tetrabromophenol blue, pyrogallol red and bis (3',3"-diiodo-4',4"-dihydroxy-5',5"-dinitrophenyl)-3,4,5,6-tetrabromo sulfonephthalein dye (DIDNTB). Electrophoresis on a variety of substrates has been used to isolate albumin from the other proteins and then staining of the albumin fraction followed by clearing and densitometry. Examples of dyes used here are ponceau red, crystal violet, amido black. For low concentrations of protein, i.e., in the range of <10 mg/L albumin, immunological assays such as immunonephelometry are often used.

Such multi-step analyses can be transferred to the chips of the invention with the reagent wells being provided with appropriate reagents to carry out the desired analysis.

Separation steps are possible in which an analyte is reacted with reagent in a first well and then the reacted reagent is directed to a second well for further reaction. In addition a reagent can be re-suspended in a first well and moved to a second well for a reaction. An analyte or reagent can be trapped in a first or second well and a determination of free versus bound reagent be made.

The determination of a free versus bound reagent is particularly useful for multizone immunoassay and nucleic acid assays. There are various types of multizone immunoassays that could be adapted to this device. In the case of adaption of immunochromatography assays, reagents filters are placed into separate wells and do not have to be in physical contact as chromatographic forces are not in play. Immunoassays or DNA assay can be developed for detection of bacteria such as Gram negative species (e.g. *E. Coli, Entereobacter, Pseudomonas, Klebsiella*) and Gram positive species (e.g. *Staphylococcus Aureus, Entereococc*). Immunoassays can be developed for complete panels of proteins and peptides such as albumin, hemoglobin, myoglobulin, α-1-microglobulin, immunoglobulins, enzymes, glyoproteins, protease inhibitors and cytokines. See, for examples: Greenquist in U.S. Pat. No. 4,806,311, Multizone analytical Element Having Labeled Reagent Concentration Zone, Feb. 21, 1989, Liotta in U.S. Pat. No. 4,446,232, Enzyme Immunoassay with Two-Zoned Device Having Bound Antigens, May 1, 1984.

Potential Applications where dried reagents are resolubilized include, filtration, sedimentation analysis, cell lysis, cell sorting (mass differences), and centrifugal separation.

Enrichment (concentration) of sample analyte on a solid phase (e.g. microbeads) can be used to improved sensitivity. The enriched microbeads could be separated by continuous centrifugation. Multiplexing can be used (e.g. metering of a variety of reagent chambers in parallel and/or in sequence) allowing multiple channels, each producing a defined discrete result. Multiplexing can be done by a capillary array compromising a multiplicity of metering capillary loops, fluidly connected with the entry port, or an array of dosing channels and/or capillary stops connected to each of the metering capillary loops. Combination with secondary forces such as magnetic forces can be used in the chip design. Particle such as magnetic beads used as a carrier for reagents or for capturing of sample constituents such as analytes or interfering substances. Separation of particles by physical properties such as density (analog to split fractionation).

EXAMPLE 1

A multiple channel device was made in a plastic chip having an annular shape using diamond bit drills and lasers. Six reaction channels were arrayed on each side of a central inlet well in an arrangement similar to that of FIG. 2. The inlet well had a volume of 37 µL, each metering well and reaction well had a volume of 1 µL, and the waste well held 37 µL. The capillary passageways were 30 µm wide and 30 µm deep. All of the wells and capillary channels were made by hydrophilic by plasma activation or polymerization. Each of the wells was vented to allow air to escape as liquid fills the space. A hydrophilic capillary stop was added at the outlet of the metering well and the reaction wells to prevent flow through the connecting capillary passageways until sufficient centrifugal force is applied. A 20 µL sample of urine was placed in the inlet well from which it wicked into the capillaries 11 and then into the individual metering or reaction wells 12a–j by capillary forces. The flow was stopped at capillary stops 14a–j. The device was spun at three increasing speeds to move the liquid from the metering wells into the first and second reaction wells and finally into the waste well. The liquid was moved from the metering well into the first reaction well at a speed of 700 rpm, then from the first reaction well into the second reaction well at 1,300 rpm, and finally from the second reaction well into the waste well at 2,500 rpm. It was found that each of the twelve channels had transferred the sample liquid from the metering well through the reaction wells and into the waste well.

EXAMPLE 2

FIG. 12 illustrates an alternative configuration similar to FIG. 2 except that each of the metering wells 12a–f are used to supply a portion of their sample to each of five reaction wells e.g. 13a to 13f. From each of these reaction wells is metered five additional portions 14a–f (1–5) to each of five more reaction wells 15a–f (1–5). In one application, 12a meters 2 μL of the specimen into the 13a reaction area, which contains 10 μL of lysis buffer. A lithum salt in the lysis buffer, as described in U.S. Pat. No. 5,258,311 causes the red blood cells to lysis and allows antibodies to react with the glycated peptides of hemoglobin. Five additional aliquotes of 0.3 μL are metered by 14a (1–5) into separate reaction areas 15a (1–5) for detection of HbAlc by measurement of agglutination of immuno reagents, as described U.S. Pat. No. 5,372,918.

What is claimed is:

1. A multi-purpose microfluidic device for analyzing a defined volume of a biological fluid sample comprising:
    (a) a sample well for receiving said sample;
    (b) at least two metering wells in fluid communication with said sample well, each of said metering wells defining the volume of said sample to be analyzed;
    (c) at least one hydrophilic capillary passageway having a width of about 10–500 μm and a depth of at least 5 μm fluidly communicating with said sample well of (a) for transferring said sample from said sample well to each one of said at least two metering wells of (b) by capillary action;
    (d) a reagent well in fluid communication with each one of said at least two metering wells through a hydrophilic capillary passageway having a width of about 10–500 μm and a depth of at least 5 μm;
    (e) a hydrophilic or hydrophobic capillary stop disposed within each of said capillary passageways of (d) each of, said capillary stops having an inlet from said capillary passageway and an outlet into said capillary passageway and disposed within said capillary passageway with a portion of said capillary passageway extending from the outlet of said capillary stop to said reagent well;
    (f) optionally at least one conditioning well for conditioning said volume of said sample in fluid communication through a first hydrophilic capillary passageway by capillary action with one of said reagent wells and through a second hydrophilic capillary passageway by capillary action with one of said metering wells of (b);
    (g) optionally at least one waste well for receiving portions of said sample of (a) from said reagent wells of (d);
    (h) sufficient vent channels for venting air to atmosphere from said metering wells of (b), said reagent well(s) of (d), and said conditioning well(s) of (f);
and wherein said sample well of (a), said metering wells of (b), said reagent wells of (d) the conditioning wells of (f), said vent channels of (h), and said capillary stop of (e) are positioned on a flat chip and capillary passageways are formed in said chip connecting said wells to each other and said wells to said vent channels, thereby providing a device for analyzing said biological fluid sample, and wherein the hydrophilicity of said capillaries of (c) and (d), is adjusted for use with said biological sample.

2. A multi-purpose device of claim 1, wherein said capillary stop of (e) is a hydrophilic stop.

3. A multi-purpose device of claim 1, wherein said capillary stop of (e) is a hydrophobic stop.

4. A multi-purpose device of claim 1, wherein the volume of said sample of (b) is about 0.3 to 2.0 μL.

5. A multi-purpose device of claim 1, wherein said sample is a member of the group consisting of blood, urine, water, saliva, spinal fluid, intestinal fluid, food, and blood plasma.

6. A multi-purpose device of claim 1, wherein said sample is assayed for a protein, a cell, a small organic molecule, or a metal.

7. A multi-purpose device of claim 6 wherein said protein is selected from the group consisting of albumin, HbAlc, protease, protease inhibitor, CRP, esterase, and BNP.

8. A multi-purpose device of claim 6 wherein said cell is selected from the group consisting of *E. Coli*, pseudomonas, white blood cells, red blood cells, *h.pylori*, strep a, chlamdia, and mononucleosis.

9. A multi-purpose device of claim 8 wherein said metal is selected from the group consisting of iron, manganese, sodium, potassium, lithium, calcium and magnesium.

10. A multi-purpose device of claim 1 further comprising a conditioning well or a reagent well disposed between said sample well and at least one of said at least two metering wells for preconditioning or pre-reacting said sample, said conditioning well or reagent well being disposed within one of said at least one capillary pass ageways of (c).

11. A multi-purpose device of claim 1 wherein at least one of said metering wells is supplied with a liquid reagent.

12. A multi-purpose device of claim 1 wherein a sample metered in one metering well of (b) is divided into secondary samples in secondary metering wells.

13. A multi-purpose device of claim 1 wherein said reagent wells contain reagents disposed on carners.

14. A multi-purpose device of claim 1 wherein one of said reagent wells of (d) is in fluid communication through an additional capillary passageway with an additional reagent well for receiving at least a portion of the sample in said reagent well and a capillary stop is disposed within said additional capillary passageway.

15. A multi-purpose device of claim 1 further comprising a reagent well for supplying liquid reagent to one of said reagent wells of (d) or to one of said metering wells of (b) through an additional capillary passageway.

16. A multi-purpose microfluidic device for analyzing a defined volume of a biological fluid sample comprising:
    (a) a sample well for receiving said sample;
    (b) at least two metering wells in fluid communication with said sample well, each of said metering wells defining the volume of said sample to be analyzed;
    (c) at least one hydrophilic capillary passageway having a width of about 10–500 μm and a depth of at least 5 μm fluidly communicating with said sample well of (a) for transferring said sample from said sample well to each one of said at least two metering wells of (b) by capillary action;
    (d) one reagent well in fluid communication with said at least two metering wells through hydrophilic capillary passageways having a width of about 10–500 μm and a depth of at least 5 μm;
    (e) a hydrophilic or hydrophobic capillary stop disposed within each of said capillary passageways of (d), each of said capillary stops having an inlet from said capillary passageway and an outlet into said capillary passageway and disposed within said capillary passageway with a portion of said capillary passageway extending from the outlet of said stop to said reagent well;
(f) optionally at least one conditioning well for conditioning said volume of said sample in fluid communication through a first hydrophilic capillary passageway by capillary action with one of said reagent wells and through a second hydrophilic capillary passageway by capillary action or with one of said metering wells of (b); (g)
optionally at least one waste well for receiving portions of said sample of (a) from said one reagent well of (d);
(h) sufficient vent channels for venting air to atmosphere from said metering wells of (b), said reagent well of (d), and said conditioning well(s) of (f);
and wherein said sample well of (a), said metering wells of (b), said reagent well of (d) and the conditioning well(s) of (f), said vent channels of (h), and said capillary stop of (e) are positioned on a flat chip and capillary passageways are formed in said chip connecting said wells to each other and said wells to said vent channels, thereby providing a device for analyzing said biological fluid sample, and wherein the hydrophilicity of said capillaries of (c) and (d) is adjusted for use with said biological sample.

17. A multi-purpose device of claim 16, wherein said capillary stop of (e) is a hydrophilic stop.

18. A multi-purpose device of claim 1, wherein said capillary stop of (e) is a hydrophobic stop.

19. A multi-purpose device of claim 16, wherein the volume of said sample of (b) is of about 0.3 to 2.0 µL.

20. A multi-purpose device of claim 16, wherein said sample is a member of the group consisting of blood, urine, water, saliva, spinal fluid, intestinal fluid, food, and blood plasma.

21. A multi-purpose device of claim 1, wherein said sample is assayed for a protein, a cell, a small organic molecule, or a metal.

22. A multi-purpose device of claim 21 wherein said protein is selected from the group consisting of albumin, HbAlc, protease, protease inhibitor, CRP, esterase, and BNP.

23. A multi-purpose device of claim 21 wherein said cell is selected from the group consisting of *E. Coli*, pseudomonas, white blood cells, red blood cells, *h.pylori*, strep a, chlamdia, and mononucleosis.

24. A multi-purpose device of claim 21 wherein said metal is selected from the group consisting of iron, manganese, sodium, potassium, lithium, calcium and magnesium.

25. A multi-purpose device of claim 16 further comprising a conditioning well or a reagent well disposed between said sample well and at least one of said at least two metering wells for preconditioning or pre-reacting said sample, said conditioning well or reagent well being disposed within one of said at least one capillary passageways of (c).

26. A multi-purpose device of claim 16 wherein at least one of said metering wells is supplied with a liquid reagent.

27. A multi-purpose device of claim 16 wherein a sample metered in one metering well of (b) is divided into secondary samples in secondary metering wells.

28. A multi-purpose device of claim 16 wherein said reagent wells contain reagents disposed on carriers.

29. A multi-purpose device of claim 16 wherein said reagent well of (d) is in fluid communication through an additional capillary passageway with an additional reagent well for receiving at least a portion of the sample in said reagent well and a capillary stop is disposed within said additional capillary passageway.

30. A multi-purpose device of claim 16 further comprising a reagent well for supplying liquid reagent to one of said reagent wells of (d) or to one of said metering wells of (b) through an additional capillary passageway.

* * * * *